United States Patent
Hackler

(10) Patent No.: US 8,457,735 B2
(45) Date of Patent: Jun. 4, 2013

(54) FIELD CONTROLLING ELECTRODE

(75) Inventor: Walter A. Hackler, Newport Beach, CA (US)

(73) Assignee: Axelgaard Manufacturing Co., Ltd, Fallbrook, CA (US)

( * ) Notice: Subject to any disclaimer, the term of this patent is extended or adjusted under 35 U.S.C. 154(b) by 22 days.

(21) Appl. No.: 13/196,094

(22) Filed: Aug. 2, 2011

(65) Prior Publication Data

US 2013/0035731 A1    Feb. 7, 2013

(51) Int. Cl.
*A61N 1/00*    (2006.01)

(52) U.S. Cl.
USPC ............................................................. 607/2

(58) Field of Classification Search
USPC .................................................... 607/2
See application file for complete search history.

(56) References Cited

U.S. PATENT DOCUMENTS

| | | |
|---|---|---|
| 4,381,789 A | 5/1983 | Naser et al. |
| 5,782,874 A * | 7/1998 | Loos ................................. 607/2 |
| 5,904,712 A | 5/1999 | Axelgaard |
| 6,745,082 B2 | 6/2004 | Axelgaard |
| 7,324,847 B2 | 1/2008 | Axelgaard |
| 7,407,503 B2 | 8/2008 | DiFrancesco |

* cited by examiner

*Primary Examiner* — George Manuel
(74) *Attorney, Agent, or Firm* — Hackler Daghighian & Martino

(57) ABSTRACT

A therapeutic device for application to a user's body in order to effect transcutaneous nerve and/or muscle stimulation, includes a conductive flexible member having a top side and a bottom side, a first electrode disposed in the member and connectable with external electrical apparatus for establishing a current distribution through the member and into the user's body, a second electrode disposed in the member and connectable with external electrical apparatus for establishing an electric field within the member in order control the current distribution through the member and into the user's body; and a conductive adhesive disposed on the conductive member bottom side for adhering the device to a the user's body.

17 Claims, 2 Drawing Sheets

FIELD CONTROLLING ELECTRODE

The present invention generally relates to a therapeutic device for application to a user's body in order to effect transcutaneous nerve and/or muscle stimulation.

Medical electrodes must provide an even electrical coupling to a patient's skin over an entire surface of the electrode to effect proper coupling. Because of the curvaceous nature of the human body, it is apparent that medical electrodes for use thereon must be flexible not only for confirmation with a patient's skin contours, but also to accommodate relative movement of the patient's skin.

A number of electrode designs have been developed using various conductive materials in order to provide electrode with controlled current distribution. As an example, U.S. Pat. No. 5,038,796, "Electrode Stimulation Electrode with Impedance Compensation" to Axelgaard teaches the use of an electrical shunt for controlling impedance composition.

No attempt has been made to date to electronically control current distribution within a therapeutic device utilizing multiple electrodes.

SUMMARY OF THE INVENTION

A therapeutic device for application to a user's body in order to effect transcutaneous nerve and/or muscle stimulation generally includes a conductive flexible member having a top side and a bottom side along with a first electrode disposed in the member and connectable with an external electrical apparatus for establishing a current distribution through the member and into the user's body.

A second electrode is provided and disposed in the member and connectable with external electrode apparatus for establishing an electric field within the member in order to control current distribution through the member and into the user's body. A conductive adhesive is disposed on the conductive member bottom side for adhering a device to the patient's body.

More particularly, the first and second electrodes are spaced apart from one another and may be placed on the conductive member top side and bottom side respectively.

Each of the electrodes may comprise a conductive grid, such as, for example, conductive ink patterns or the like.

The second electrode produces an electric field caused in part by a voltage difference between the first and second electrodes which can be used to alter, modify, or control the current distribution through the member provided by the first electrode.

BRIEF DESCRIPTION OF THE DRAWINGS

The advantages and features of the present invention will be better understood by the following description when considered in conjunction with the accompanying drawings, in which.

DETAILED DESCRIPTION

Figure 1:
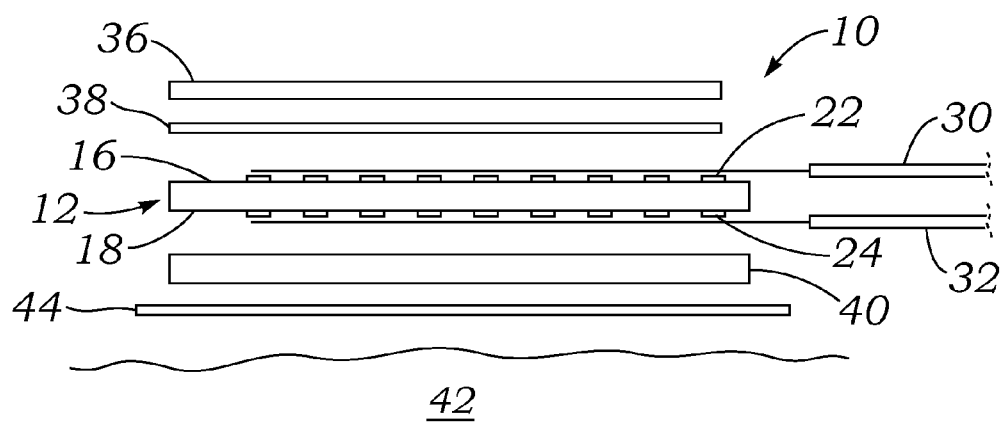
FIG. 1 is an exploded cross sectional view of a therapeutic device in accordance with the present invention generally showing a conductive flexible member having a top side and a bottom side, a first electrode disposed in the member and connectable within an external electrical apparatus for establishing a current distribution through the member and into a user's body (not shown) along with a second electrode disposed in the member and connectable with an external electrical apparatus for establishing an electrical field within a member in order to control the current distribution through the member and into the user's body.
Figure 2A:
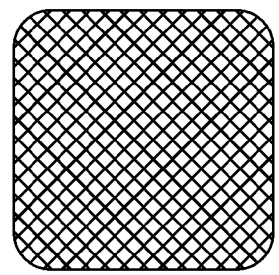
FIGS. 2a-2d illustrate various patterns which may be useful for providing a conductive grid.
Figure 2B:
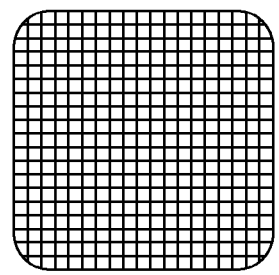
Figure 2C:
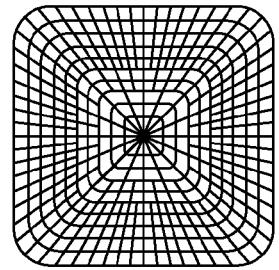
Figure 2D:
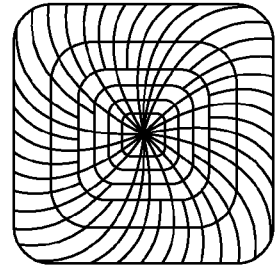

With reference to FIG. 1, there is shown a therapeutic device 10 in accordance with the present invention which generally includes a conductive flexible member 12 having a top side 16 and a bottom side 18, a pair of transversely spaced apart electrodes, namely a first electrode 22 and a second electrode 24 disposed in or on the conductive flexible member 12 with both electrodes 22, 24 being connectable, through lead wires 30, 32 to external electrical apparatus (not shown).

A non-conductive flexible sheet 36 covers the conductive flexible member 12 and is adhered thereto by an adhesive layer 38. A suitable conductive hydrogel adhesive 40 is utilized for adhering a device 10 to a patient's body or skin 42.

A plastic carrier 44 may be provided in order to prevent inadvertent and/or premature adhesion of the patient's skin 42 or other object to the hydrogel 40 with the carrier 44 being removed prior to application of the device 10 to the patient's skin.

The conductive flexible member 12 may be formed from PVC and the electrodes 22, 24 may have a grid pattern formed by a conductive ink such as illustrated in FIGS. 2a-2d. Various patterns, as illustrated in FIGS. 2a-2h, among others, may be utilized for the electrodes 22, 24 in order to tailor current distribution of the device 10.

Various electrical stimulation pulses of different voltages may be applied to the electrodes 22, 24 through the leads 30, 32.

A current distribution provided by the first electrode 22 and the skin 42 is altered by the electric field established by the electrification of the second electrode 24. Thus, control of the current distribution through the member 12 and into the user's body or skin 42 is effected.

Not being bound by theory of operation the field controlling electrode may operate analogous to a triode.

The relative conductivities of the conductive flexible member 12 and electrodes 22, 24 also contribute to the current density control with the conductivity of the grid electrodes 22, 24 being greater than the conductivity of the flexible sheet 12.

Although there has been hereinabove described a specific dual-sided CC electrode in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. A therapeutic device for application to a user's body in order to effect transcutaneous nerve and/or muscle stimulation, the device comprising:
    a conductive flexible member having a top side and a bottom side;
    a first electrode disposed in the member and connectable with external electrical apparatus for establishing a current distribution through the member and into the user's body;

a second electrode disposed in the member and connectable with external electrical apparatus for establishing an electric field within the member in order control the current distribution through the member and into the user's body; and a conductive adhesive disposed on the conductive member bottom side for adhering the device to a the user's body.

2. The device according to claim 1 wherein said first electrode is disposed at the flexible member top side.

3. The device according to claim 2 wherein said second electrode is disposed at the flexible member bottom side.

4. The device according to claim 1 wherein the first and second electrodes are spaced apart from one another.

5. The device according to claim 4 wherein at least one of the first and second electrodes comprises a conductive grid.

6. The device according to claim 4 wherein the first and second electrodes each comprises a conductive grid.

7. The device according to claim 1 wherein each conductive grid comprises a conductive ink pattern.

8. The device according to claim 7 wherein the ink pattern has a greater conductivity than a conductivity of the flexible member.

9. A therapeutic device for application to a user's body in order to effect transcutaneous nerve and/or muscle stimulation, the device comprising:

a conductive flexible member having a top side and a bottom side;

a pair of transversely spaced apart electrodes disposed on or in said flexible conductive member for controlling, in combination, electrical current density applied to the user's body, each electrode having a connection for establishing electrical contact with external apparatus, wherein one of the pair of electrodes is configured to establish a current distribution through the member and another of the pair of electrodes is configured to establish an electric field within the member; and a conductive adhesive disposed on the conductive member bottom side for adhering the device to the user's body.

10. The device according to claim 9 wherein one of the pair of electrodes is disposed on the conductive member top side and another of the pair of electrodes is disposed on the conductive member bottom side.

11. The device according to claim 9 wherein each of the pair of electrodes comprises a conductive pattern.

12. The device according to claim 9 wherein at least one of the electrodes comprises a conductive grid.

13. The device according to claim 9 wherein the electrodes each comprise a conductive grid.

14. The device according to claim 13 wherein each conductive grid comprises a conductive ink pattern.

15. The device according to claim 14 wherein the ink pattern comprises a greater conductivity than a conductivity of the flexible member.

16. The device according to claim 9 wherein one of the pair of electrodes is disposed at the flexible member top side.

17. The device according to claim 16 wherein another of the pair of said second electrodes is disposed at the flexible member bottom side.

* * * * *

UNITED STATES PATENT AND TRADEMARK OFFICE
CERTIFICATE OF CORRECTION

| | | |
|---|---|---|
| PATENT NO. | : 8,457,735 B2 | Page 1 of 1 |
| APPLICATION NO. | : 13/196094 | |
| DATED | : June 4, 2013 | |
| INVENTOR(S) | : Walter A. Hackler | |

It is certified that error appears in the above-identified patent and that said Letters Patent is hereby corrected as shown below:

In the Claims:

Column 3, line 3: insert the word -- to -- before "control"

Column 3, line 7: delete the word "a" after "to"

Column 4, line 27: delete "said second"

Signed and Sealed this
Thirtieth Day of July, 2013

Teresa Stanek Rea
*Acting Director of the United States Patent and Trademark Office*